(12) United States Patent
Bayer et al.

(10) Patent No.: US 9,253,889 B2
(45) Date of Patent: Feb. 2, 2016

(54) METHOD OF GROWING ELECTRICALLY CONDUCTIVE TISSUE

(71) Applicants: Eben Bayer, Troy, NY (US); Gavin McIntyre, Troy, NY (US)

(72) Inventors: Eben Bayer, Troy, NY (US); Gavin McIntyre, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 211 days.

(21) Appl. No.: 14/021,099

(22) Filed: Sep. 9, 2013

(65) Prior Publication Data

US 2014/0097008 A1   Apr. 10, 2014

Related U.S. Application Data

(60) Provisional application No. 61/697,976, filed on Sep. 7, 2012.

(51) Int. Cl.
| | |
|---|---|
| *H05K 1/00* | (2006.01) |
| *H05K 3/00* | (2006.01) |
| *H05K 1/03* | (2006.01) |
| *H01L 51/00* | (2006.01) |
| *C12N 1/14* | (2006.01) |
| *C12P 1/02* | (2006.01) |
| *C12P 3/00* | (2006.01) |

(52) U.S. Cl.
CPC ............... *H05K 3/0011* (2013.01); *C12N 1/14* (2013.01); *C12P 1/02* (2013.01); *C12P 3/00* (2013.01); *H01L 51/0093* (2013.01); *H05K 1/0353* (2013.01); *H05K 1/0366* (2013.01); *H05K 2203/122* (2013.01); *H05K 2203/178* (2013.01)

(58) Field of Classification Search
USPC .......................... 174/258, 250, 253–257, 260
See application file for complete search history.

(56) References Cited

U.S. PATENT DOCUMENTS 5,030,425 A * 7/1991 Bowers-Irons et al. ......... 423/87
6,475,811 B1 * 11/2002 Babcock ............................ 438/1

* cited by examiner

*Primary Examiner* — Tremesha S Willis
(74) *Attorney, Agent, or Firm* — Francis C. Hand; Carella, Byrne, Et Al

(57) ABSTRACT

An electrical circuit is comprised of a sheet of mycelium having a wiring pattern for an electrical circuit thereon. The sheet of mycelium is prepared from a solution of Potato Dextrose Broth and Potato Dextrose Agar that is inoculated with a macerated tissue culture including a filamentous fungi selected from the group consisting of Basidiomycota, Ascomycota and Zygomycota. A sheet of tissue that grows on the surface of the solution is extracted, plasticized and dried prior to being formed with the wiring pattern.

6 Claims, 5 Drawing Sheets

METHOD OF GROWING ELECTRICALLY CONDUCTIVE TISSUE

Figure 1:
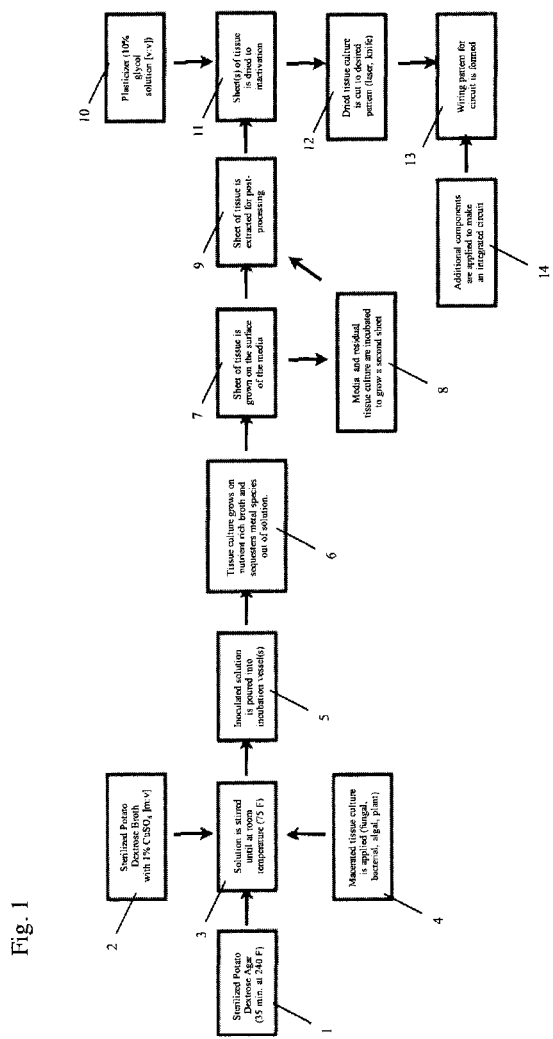

This application claims the benefit of Provisional patent application No. 61/697,976 filed Sep. 7, 2012.

Filamentous fungi are among many eukaryote and prokaryote species found to sequester metal ions and salts from their surrounding environments. Fungal species have developed multiple pathways to inactivate free radicals and accumulate the ion species either within the cell (chelation) or on the exterior of the cell wall (biosorption). The fungal cell wall, which is comprised predominately of chitin, chitosan, and glucans is dielectric and serves as a natural electrical insulator. These biopolymers offer a high resistance to an electrical current and significant voltage drops are measured when dried tissue is connected to a multimeter and source (3V, from two D cell batteries).

Filamentous fungal species, including the ascomycete *Penicillium orcho-chloron*, have been found to accumulate metal species, such as copper on phosphoryl and carboxyl groups associated with the primary amine of the aforementioned amino sugar polymers. The biosorption of these metal species is retained after the tissue is dried, and the resultant tissue culture has been found to become more electrically conductivity.

For example, *P. orcho-chloron* was grown on potato dextrose agar (PDA), plasticized with a 10% glycerol solution and dried in a convection dryer. When connected to a 3V source, the resistance of the mycelium dropped the voltage to 180 mV.

*P. orcho-chloron* was grown on potato dextrose agar (PDA) supplemented with 1000 ppm of $CuSO_4$ plasticized with a 10% glycerol solution and dried in a convection dryer. When connected to a 3V source, the resistance of the mycelium dropped the voltage to 2.25V.

The electrical resistivity of the mycelium has been observed to decline with increasing concentrations of cupric sulfate ($CuSO_4$) or aluminum oxide ($Al_2O_2$) in the growth media. Thus, as the concentrations of metal species increases and is absorbed to the fungal cell wall the biopolymer's conductivity increases. This ability to vary the resistivity of the material with some precision based on metal specie concentration in the growth media (liquid, agarose gel) allows for certain segments of the tissue (even individual hyphae or branches of cells) to serve as a resistor.

Accordingly, it is an object of the invention to fabricate a simple circuit from mycelium.

It is another object of the invention to fabricate an electrical circuit from mycelium with variable characteristics.

Briefly, the invention provides a simple circuit grown of mycelium with a concentration of a metal species.

The invention also provides a more complex circuit, such as a whetstone bridge, with a variation in the concentration of a metal species in segmented quadrants (similar to the standard "X-plate" used in cell culture laboratories).

Filamentous fungi are not the only organisms with this ability and other life applicable to this process include:

(1) Yeasts, budding and dimorphic species of fungi, have been found to grow in lake water (Butte, Mont.) contaminated with metal species. The fungus has the ability to sequester 80-90% of cupric sulphate ($Cu^{2+}$) found in a controlled volume of lake water.

(2) Algae grown in a metal rich solution in a similar method as (1), forming a colony unit, which can be post processed or grown to net-shape.

(3) Bacteria grown in a metal rich solution and used in a similar method as (1), and could be induced to grow into microstructures such as honeycombs (*Bacillus thurengensis*).

(4) Germinating pollen tubes from non-angiosperm plants could also serve as a linear cell formation that could be stimulated to grow directionally.

In one embodiment, the method of making an electrical circuit comprising the initial steps of obtaining a sterilized Potato Dextrose Broth containing a metal salt; obtaining a sterilized Potato Dextrose Agar; and adding the sterilized Potato Dextrose Broth to said sterilized Potato Dextrose Agar to obtain a solution.

Thereafter, the obtained solution is inoculated with a macerated tissue culture including a filamentous fungi selected from the group consisting of Basidiomycota, Ascomycota and Zygomycota.

Next, the inoculated solution is poured into at least one incubation vessel for a time sufficient for a tissue culture to grow across a top surface of the solution while sequestering the metal salt and creating a sheet of tissue.

The sheet of tissue is then extracted from the solution, a plasticizer is added to the sheet of tissue and the sheet dried.

A wiring pattern for an electrical circuit is then formed in the dried sheet.

Additional components may also be applied to the dried sheet of tissue to make an integrated circuit.

Also, a plurality of said sheets of tissue may be obtained and stacked prior to forming a wiring pattern in a topmost sheet of the stack.

Figure 2:
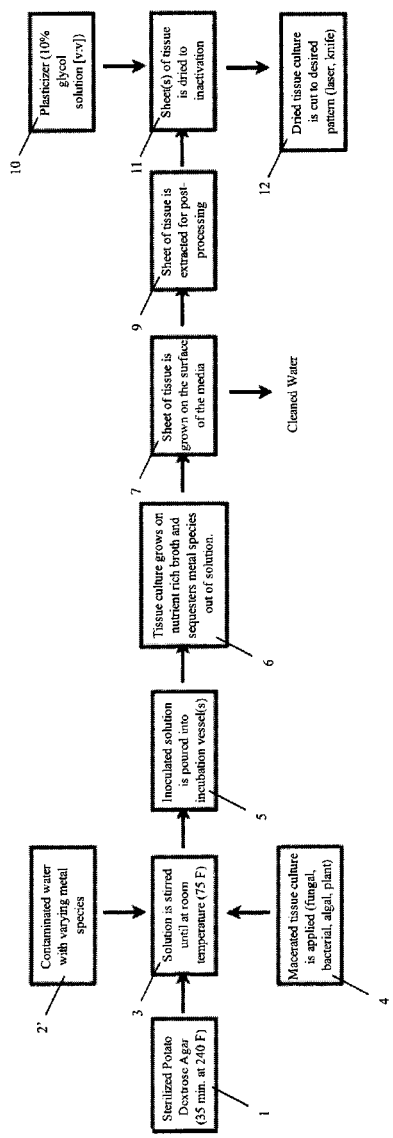
Figure 3:
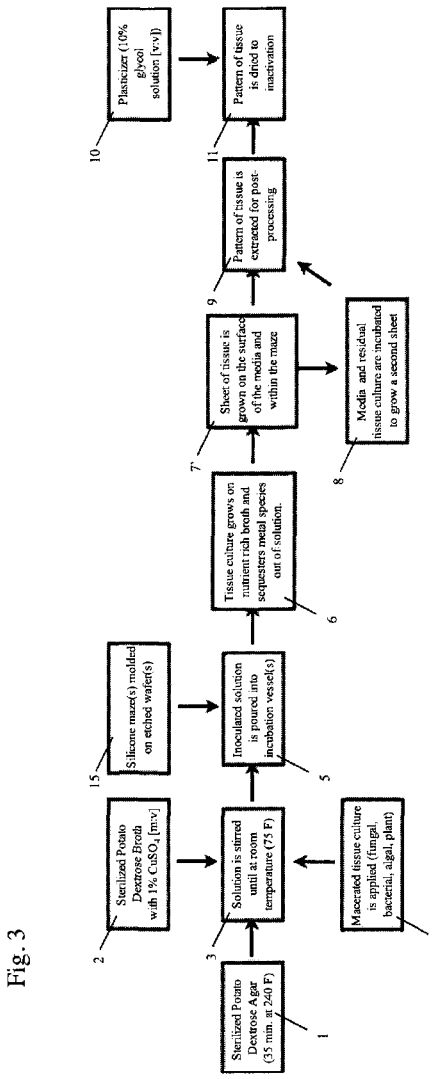
Figure 4:
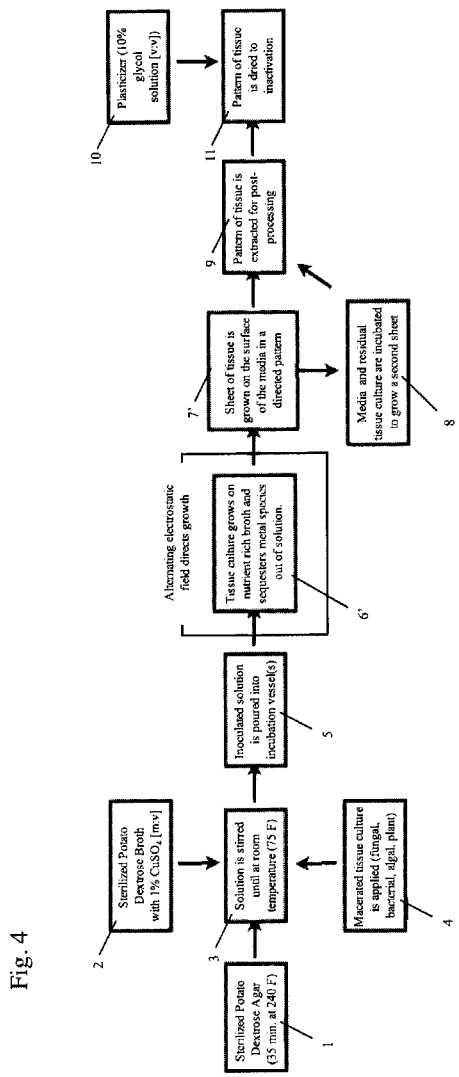
Figure 5:
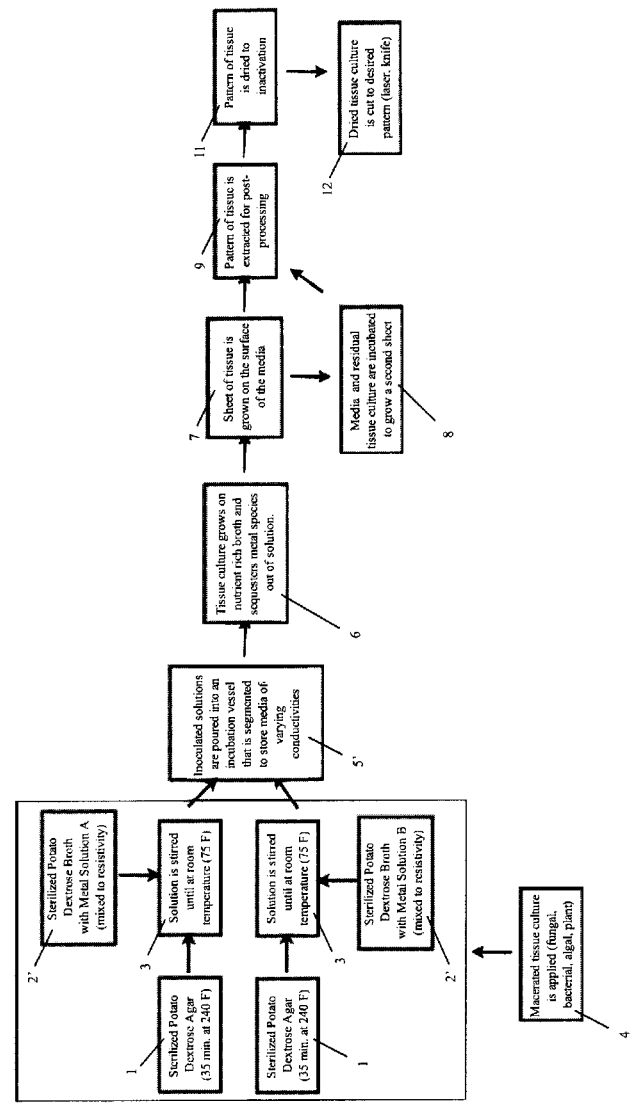

These and other objects and advantages of the invention will become more apparent from the following detailed description taken in conjunction with the accompanying drawings wherein:

FIG. 1 schematically illustrates a process for making an electrical circuit in accordance with the invention;

FIG. 2 schematically illustrates a process as in FIG. 1 using a contaminated water supply;

FIG. 3 schematically illustrates a process as in FIG. 1 using a silicone maze;

FIG. 4 schematically illustrates a process as in FIG. 1 using an alternating electrostatic field to direct growth; and FIG. 5 schematically illustrates a modified process for making a dried tissue culture from which an electrical circuit may be made in accordance with the invention.

Referring to FIG. 1, in order to make an electrical circuit, a filamentous fungi from three of the principle phyla (Basidiomycota, Ascomycota Zygomycota) were selected for growth in a culture media.

Dehydrated culture media, for example, Difco Brand Potato Dextrose Agar (PDA) and Difco Brand Potato Dextrose Broth (PDB) were obtained from Becton-Dickinson of New Jersey. Each culture media was sterilized separately in an autoclave for 35 minutes at 15 psi and 240 F. °. [steps 1 and 2]

900 ml of the PDA was prepared and 100 ml of the PDB was prepared. The PDB contained the entirety of the metal specie, such as $CaSO_4$, $CuCl_2$; and $Al_2O_2$. In the present example, a 1% $CuSO_4$ [m:v] media was used, i.e. 10 g of the salt placed in the 100 mL solution of the PDB.

The solutions were both stirred on magnetic stir plates at 150 rpm until all media constituents were fully solubilized.

Once sterilized, the media was brought to near room temperature (75°) while being stirred on a magnetic stir plate in a laminar flow. Once the media became cool to the touch, the PDB containing the metal was poured into the stirring PDA.

This prevented the alginate from chelating the metal, allowing the ion or metal salt to agglomerate onto the exterior of the fungal cell wall. [step 3]

Prior to setting, the agarose media was poured into individual Petri dishes. This procedure resulted in a solid media that could be inoculated with either a single mycelium inoculation point transferred from an older agarose gel culture or the like, a spore mass suspension, or macerated mycelium homogenized in a laboratory blender. In the present example, a macerated tissue culture (fungal, bacterial, algal, plant) was added to the solution in the Petri dishes. [step 4]

Next, the inoculated solution was poured into incubation vessels. [step 5]

Under these methods, a tissue culture (mycelium) grew across the top surface of the nutrient rich broth (agarose gel) while sequestering the metal species and creating a sheet of tissue (mycelium). [steps 6 and 7]

The media and residual tissue culture were incubated to grow a second sheet and added to the first sheet. [step 8]

Both sheets of tissue (mycelium) were extracted from the media for post-processing [step 9] and a plasticizer, e.g. a 10% glycol solution [v:v] was added to the sheets [step 10].

Thereafter, the sheet(s) were dried to inactivation [step 11] and subsequently cut to a desired pattern, for example by knife or laser. [step 12]

The resultant cut sheet was formed with a wiring pattern for an electrical circuit [step 13] with additional components applied to make an integrated circuit [step 14].

Referring to FIG. 2, wherein like steps are indicated by like step numbers, the PDB was prepared with water contaminated with a roughly known concentration of metal salts and ions [step 2'] Such water could be derived from a Superfund site that requires remediation.

In addition, the water cleansed of the metal species was removed from step 7.

A viscous liquid suspension can be produced in a similar manner by preparing 900 mL of PDB (FIG. 1), replacing the PDA, that contains 0.3% [m v] agar agar to support macerated or carried (residing on a particle) mycelium. The components are mixed during the same temperature interval, but continuously stirred by the magnetic stir plate until the solution is uniformly at room temperature. This prevents the metal salts from settling out of solution.

Once cool, the fungal tissue can be poured into the metal enriched media within a liquid or on a solid carrier (millet). This will suspend the mycelium within the fluid and allow the hyphae to radiate out from individual inoculation points in three dimensions. The media will result in a dense sheet of mycelium forming on the top surface of the broth and masses of mycelium suspended in the solution that can later be mechanically extracted (filtration, centrifugation).

The harvested mycelium, from solid or liquid media, can then be placed in intimate contact with other tissues to adhere and bind to itself, or processed as stand alone masses.

The mycelium can be chemically post-processed to grant additional performance. These include vacuum infusion of a polyol (10% glycerol solution [v:v]) to plasticize the tissue or a solution containing additional metal salts (enhance conductivity), stacking layers of untreated mycelium between conductive layers to provide electrical insulation, and immersing the materials in a phosphate solution which serves as a doping agent. The complete sheets or masses of mycelium are then dried (conductive, convection, and/or radiation) to inactivate the fungus and extract the remaining water.

The conductive mycelium, with either a static conductivity or variable conductivities based on growth media metal composition, can be cut into desired circuit patterns using a computer numerical control (CNC) laser cutter, CNC knife or hotwire cutter, and or continuous die/stamp. Or the materials could be extruded or casted in a slurry comprised of the mycelium.

Layers of mycelium could be stacked, alternating conductive and resistive layers, to create a wafer of thin, flexible circuitry.

Embedded components including light emitting diodes, diodes, capacitors, or inductors could be applied to the tissue as a post process. Similar to the variable resistance mentioned above, the capacitance may be varied within fungal cell lines or tissues.

Referring to FIG. 3, wherein like steps are indicated by like step numbers, fungal tissue (mycelium), as well as other microbial and plant species, exhibits environmental tropisms in which cell growth is stimulated by its surroundings (temperature, light, electromagnetism, chemotaxis, and the like). There are a number of methods that could allow for the growth of circuit wires and individual components (resistors, capacitors) that would leverage the scale of individual hyphae (spore tube, budding cell cluster, and the like). Fungal cells are traditionally 35 μm in length and 5 μm in diameter, but binding or branching hyphae have been found to offer even finer resolution.

In the illustrated embodiment, fungal spores or macerated fungal mycelium were injected into a silicone maze that had a width between walls of approximately 10 μm.

Etching a silicone wafer with the negative of the desired wire configuration and then pouring silicone on the wafer to cast the positive created the maze (microfluidics) that served as a growth and incubation enclosure for the fungus. [step 15]

The silicone maze was placed on top of the agarose media, which provides a solid surface, metal ions for conductivity, and nutrition for growth. [step 5] A uniform static pressure was applied in order to maintain the maze flush on the agarose gel. The gel could be segmented such that the maze is aligned with differing concentrations of metal ion species and variable conductivity performance can be achieved.

A spore syringe, or the like (vacuum), was used to inject fungal spores or macerated hyphae into intersection points within the maze. Once injected, the spores germinated, or hyphae/protoplasts grew, and followed the path of the maze due to thigmotropisms (M. Held, 2010). Once the growth was complete, the resultant tissue was post processed and dried in a manner similar to the examples of FIGS. 1 and 2.

Referring to FIG. 4, wherein like steps are indicated by like step numbers, fungal hyphae are among several organisms that exhibit polarized growth. Fungi have an organelle known as a polarisome, which directs the hyphal apex to either an anion or cation source. As such, this capability can be integrated into directing hyphal growth to form circuit patterns. The fungus could be inoculated on nutrient rich media containing the metal ion source(s) in either macerated mycelium or spore form. The growth can then be controlled in a number of ways:

1. An electron, or other ion beam, from a cathode ray tube (CRT) or the like can trace the pathways of the fungal hyphae. The beam would lead the hyphal apices and ensure mycelium branching only occurred at desired locations.
2. The fungal hyphae could also be placed in a solenoid, which would direct growth linearly. The hyphal expansion would start and the solenoid or media containing the fungus would rotate depending on the desired orientation of the circuit path.

In the illustrated embodiment, the fungus was inoculated on a media that was encompassed with electrostatic fields, i.e. an electrostatic field that directed growth. [step 6']

Electrodes on either side of the Petri dish, or other media container, could be activated depending on the location of the hyphae and the desired orientation for circuitry.

Referring to FIG. 5, wherein like steps are indicated by like step numbers, two different inoculated solutions were made. For one solution, the PDB was mixed with a metal solution A to obtain a first resistivity while for the other solution, the PDB was mixed with a metal solution B to obtain a second and different resistivity from the first resistivity. [steps 2']

Thereafter, both inoculated solutions were poured into an incubation vessel that was segmented to store media of different conductivities [step 5'] and subsequently processed as above.

In this embodiment, a plasticizer was not added.

The invention thus provides a process of fabricating a simple circuit from mycelium as well as an electrical circuit with variable characteristics from mycelium.

What is claimed is:

1. A method of making an electrical circuit comprising the steps of
    obtaining a sterilized Potato Dextrose Broth containing a metal salt;
    obtaining a sterilized Potato Dextrose Agar;
    adding the sterilized Potato Dextrose Broth to said sterilized Potato Dextrose Agar to obtain a solution;
    inoculating the solution with a macerated tissue culture including a filamentous fungi selected from the group consisting of Basidiomycota, Ascomycota and Zygomycota;
    thereafter pouring the inoculated solution into at least one incubation vessel for a time sufficient for a tissue culture to grow across a top surface of the solution while sequestering said metal salt and creating a sheet of tissue;
    extracting the sheet of tissue from the solution;
    adding a plasticizer to said sheet of tissue;
    drying said sheet of tissue; and
    subsequently forming a wiring pattern for the electrical circuit in said dried sheet of tissue.

2. A method as set forth in claim 1 further comprising the step of applying additional components to said dried sheet of tissue to make an integrated circuit.

3. A method as set forth in claim 1 wherein said metal salt is one of $CuSO_4$, $CuCl_2$ and $Al_2O_2$.

4. A method as set forth in claim 1 wherein said metal salt is $CuSO_4$.

5. A method as set forth in claim 1 wherein a plurality of said sheets of tissue are stacked and subsequently plasticized and dried prior to forming a wiring pattern in a topmost sheet of said stack.

6. An electrical circuit comprising a sheet of mycelium having a wiring pattern for the electrical circuit thereon.

* * * * *